(12) United States Patent
Katschnig et al.

(10) Patent No.: US 7,566,430 B2
(45) Date of Patent: Jul. 28, 2009

(54) APPARATUS FOR STERILIZING, PASTEURIZING, AND/OR DISINFECTING A PUMPABLE OR FREE FLOWING MEDIUM

(75) Inventors: Helmut Katschnig, Burggasse 108, 8750 Judenburg (AT); Ernst Gruber, Judenburg (AT)

(73) Assignee: Helmut Katschnig, Judenburg (AT)

( * ) Notice: Subject to any disclaimer, the term of this patent is extended or adjusted under 35 U.S.C. 154(b) by 857 days.

(21) Appl. No.: 10/950,798

(22) Filed: Sep. 27, 2004

(65) Prior Publication Data
US 2005/0063885 A1  Mar. 24, 2005

Related U.S. Application Data

(63) Continuation of application No. PCT/AT03/00089, filed on Mar. 28, 2003.

(30) Foreign Application Priority Data
Mar. 28, 2002  (AT) ................................ A 494/2002

(51) Int. Cl.
*A61L 2/04* (2006.01)
(52) U.S. Cl. .................... 422/307; 422/28; 422/905
(58) Field of Classification Search ............... 422/307, 422/38, 28, 905; 392/314, 320, 322
See application file for complete search history.

(56) References Cited

U.S. PATENT DOCUMENTS

| | | |
|---|---|---|
| 3,579,631 A | 5/1971 | Stewart, Jr. et al. |
| 4,216,879 A * | 8/1980 | McMillin ................. 222/1 |
| 5,403,564 A | 4/1995 | Katschnig et al. |
| 5,863,580 A | 1/1999 | Reznik |

FOREIGN PATENT DOCUMENTS

| | | | |
|---|---|---|---|
| AT | 399 658 B | | 6/1995 |
| JP | 2001304782 A | * | 10/2001 |

OTHER PUBLICATIONS

English Abstract for JP 2001304782 A; Inventor: Tamura et al.*

* cited by examiner

*Primary Examiner*—Sean E Conley
(74) *Attorney, Agent, or Firm*—Henry M. Feiereisen; Ursula B. Day

(57) ABSTRACT

Apparatus for sterilizing, pasteurizing, and/or disinfecting a pumpable or free-flowing medium includes at least one heating source, a temperature holding device which is monitored by means of a thermal sensor, and an outlet. The pressure required for the treatment is maintained within the temperature holding device by at least one unit conveying member in opposition to a resistance pressure. Two conduit branches are connected to a conduit located downstream of the temperature holding device. A restriction member and a shut-off member are disposed in each of the two conduit branches, with one conduit branch extending to the outlet while the other conduit branch leads to the feed conduit upstream from the heating source as a return conduit. The restriction member is hereby part of a heat exchanger which guides medium from the temperature holding device in counterflow to a flow of medium to the heating source.

5 Claims, 2 Drawing Sheets

APPARATUS FOR STERILIZING, PASTEURIZING, AND/OR DISINFECTING A PUMPABLE OR FREE FLOWING MEDIUM

CROSS-REFERENCES TO RELATED APPLICATIONS

This application is a continuation of prior filed copending PCT International application no. PCT/AT03/00089, filed Mar. 28, 2003, which designated the United States and on which priority is claimed under 35 U.S.C. §120, the disclosure of which is hereby incorporated by reference, and which claims the priority of Austrian Patent Application, Serial No. A 494/2002, filed Mar. 28, 2002, pursuant to 35 U.S.C. 119 (a)-(d).

BACKGROUND OF THE INVENTION

The present invention relates, in general, to an apparatus for sterilizing, pasteurizing, and/or disinfecting pumpable or free flowing medium.

Nothing in the following discussion of the state of the art is to be construed as an admission of prior art.

Austrian Pat. No. AT 399 658 B describes an apparatus of this type including a microwave unit forming a treatment chamber for receiving contaminated medium, and a temperature holding device for maintaining the medium at a desired temperature. A three-way valve is disposed upstream of a medium outlet and downstream of a pump and includes one port connected via a return conduit to the inlet for incoming contaminated medium. Depending on the process stage, either contaminated medium or already pasteurized, disinfected or sterilized medium is intended to flow through the conduit leading downstream of the holding device so that during change of the medium flow from return flow to outflow through appropriate actuation of the three-way valve, contaminated or insufficiently treated medium may reach the outlet.

It would therefore be desirable and advantageous to provide an improved apparatus for sterilizing, pasteurizing, and/or disinfecting a pumpable or free flowing medium to obviate prior art shortcomings and to prevent vapor formation and ingress of contaminated medium into the outlet.

SUMMARY OF THE INVENTION

According to one aspect of the present invention, an apparatus for sterilizing, pasteurizing and/or disinfecting a pumpable or free-flowing medium, includes at least one heating source receiving medium via a feed conduit, a temperature sensor for monitoring a temperature of the medium along a temperature holding device downstream of the heating source, an outlet, a conveying member moving the medium to the temperature holding device and maintaining a feed pressure in the temperature holding device, and at least two conduits routed downstream from the temperature holding device, with one of the conduits communicating with the outlet, and with the other one of the conduits constituting a return conduit for returning the medium to the feed conduit, each one of the conduits including a flow restriction member generating a resistance pressure in opposition to the feed pressure of the conveying member by restricting a passage for flow of medium, and a shutoff member for controlling a flow of fluid through the conduit, wherein the restriction member is part of a heat exchanger which guides medium from the temperature holding device in counterflow to a flow of medium to the heating source.

According to another feature of the present invention, the restriction member may include a heat exchanging coil having a flow cross section which is smaller than a flow cross section of the conduit upstream of the restriction member.

According to another feature of the present invention, a flowmeter may be disposed in the feed conduit. As a result, the apparatus can be operated at different flow rates so as to maintain the desired temperature of the medium within the temperature holding device for a required retention time. This is especially of relevance when different processes are involved, such as sterilizing, pasteurizing or disinfecting.

According to another feature of the present invention, a further temperature sensor may be disposed downstream of the restriction member in the conduit that leads to the outlet. In this way, the medium temperature can be monitored, when reaching the outlet, and steps can be undertaken to prevent the medium temperature from exceeding 60° C. and thereby prevent damage to outlet conduits or other downstream conduits.

According to another feature of the present invention, a pressure sensor may be disposed in a passageway between the conveying member and the restriction member, thereby providing an added monitoring option of the apparatus.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
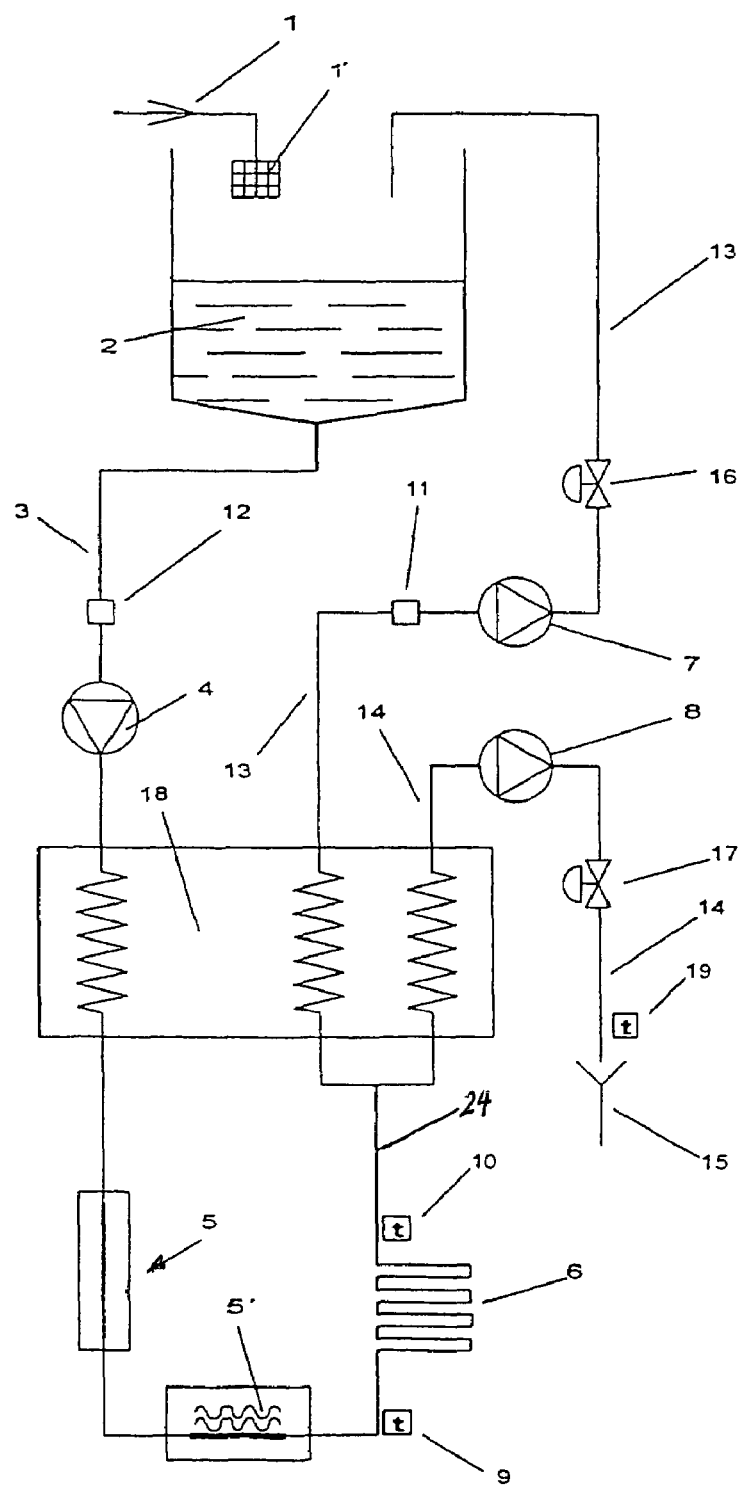
FIG. 1 is a schematic flow diagram of one embodiment of an apparatus for sterilizing, pasteurizing, and/or disinfecting pumpable or free flowing medium in accordance with the present invention.

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a schematic flow diagram of one embodiment of an apparatus for sterilizing, pasteurizing, and/or disinfecting pumpable or free flowing medium in accordance with the present invention, including a supply conduit 1 for incoming contaminated liquid medium which flows through a filter 1' into a storage tank 2. A feed conduit 3 connects a bottom discharge of the tank 2 with a pump 4 which forces medium from the tank 2 via a heating unit, generally designated by reference numeral 5, to a temperature holding device 6 of coiled configuration. The heating unit 5 may be of any suitable construction or energy source known to the artisan and may, optionally, include a microwave heater, as indicated, by way of example, by reference numeral 5'. The holding device 6 terminates in a conduit portion 24 which is split in two conduit branches 13 and 14, with the conduit branch 13 routed back to the storage tank 2, and the conduit branch 14 leading to a decontaminated medium outlet 15. Disposed in the conduit branch 13 is a pump 7, and disposed in the conduit branch 14 is a pump 8 to force medium along the intended path.

Placed upstream of the temperature holding device 6 is a heat sensor 9 and placed downstream of the temperature holding device 6 is a heat sensor 10. Both temperature sensors 9, 10 monitor the medium temperature directed through the holding device 6 to maintain the temperature constant. Provided in the conduit portion 24 upstream of the pump 7 is a pressure sensor 11 for measuring a medium pressure in an area between the pump 4 and the pump 7 and 8, respectively. A shut-off member 16 is disposed in the conduit branch 13, downstream of the pump 7, and a shut-off member 17 is disposed in the conduit branch 14, downstream of the pump 8. In this way, the flow of medium can be regulated by closing one or the other of the conduit branches 13, 14. Of course, the pumps 7, 8 may be constructed to be self-locking, i.e. the pumps 7, 8 are constructed to cut a flow through the associated conduit branches, so that the provision of shut-off members may be omitted.

Reference numeral 18 designates a heat exchanger to preheat incoming medium from the storage tank 2 and flowing to the heating unit 5, by medium exiting the temperature holding device 6.

Disposed in feed conduit 3 upstream of the pump 4 is a flowmeter for monitoring the actual medium flow rate in order to compute a retention time of the medium within the temperature holding device 6.

The apparatus operates as follows: When starting the apparatus, incoming contaminated medium is circulated by the pump 4 to flow from the storage tank 2 via the heating unit 5, temperature holding device 6, conduit branch 13, pump 7 and shut-off member 16 back to the storage tank 2. Pump 8 in conduit branch 14 is shutdown, and shut-off member 17 is closed. As a result, no medium can flow trough conduit branch 14, not even in the zone upstream of the pump 8. The apparatus is operated in this mode until the temperature sensor 9, upstream of the holding device 6, and the temperature sensor 10, downstream of the holding device 6, show a constant temperature. By means of the flowmeter 12, the required retention time of the medium to be treated in the holding device 6 is determined and controlled to a desired value by appropriately operating the pumps 4 and 7.

As soon as the desired temperature of the medium in the holding device 6 is kept constant and the desired retention time is reached, pump 7 in conduit branch 13 is shut down, and pump 8 in conduit branch 14 is operated. At the same, shut-off member 16 is closed and shut-off member 17 is opened. In both operating modes, the pressure sensor 11 ascertains the pressure in the system and thus is able to monitor the necessary pressure for maintaining the operating parameters. Suitably, a further temperature sensor 19 is disposed in conduit branch 14 in immediate proximity of the outlet 15 for monitoring the temperature of outflowing medium. The apparatus is so constructed that a temperature above 60° C., as registered by the temperature sensor 19, results in a shutdown of the apparatus or in a medium circulation, or in an activation of a further heat exchanger (not shown), so as to prevent a discharge of excessively heated medium and thereby damage to the system.

Figure 2:
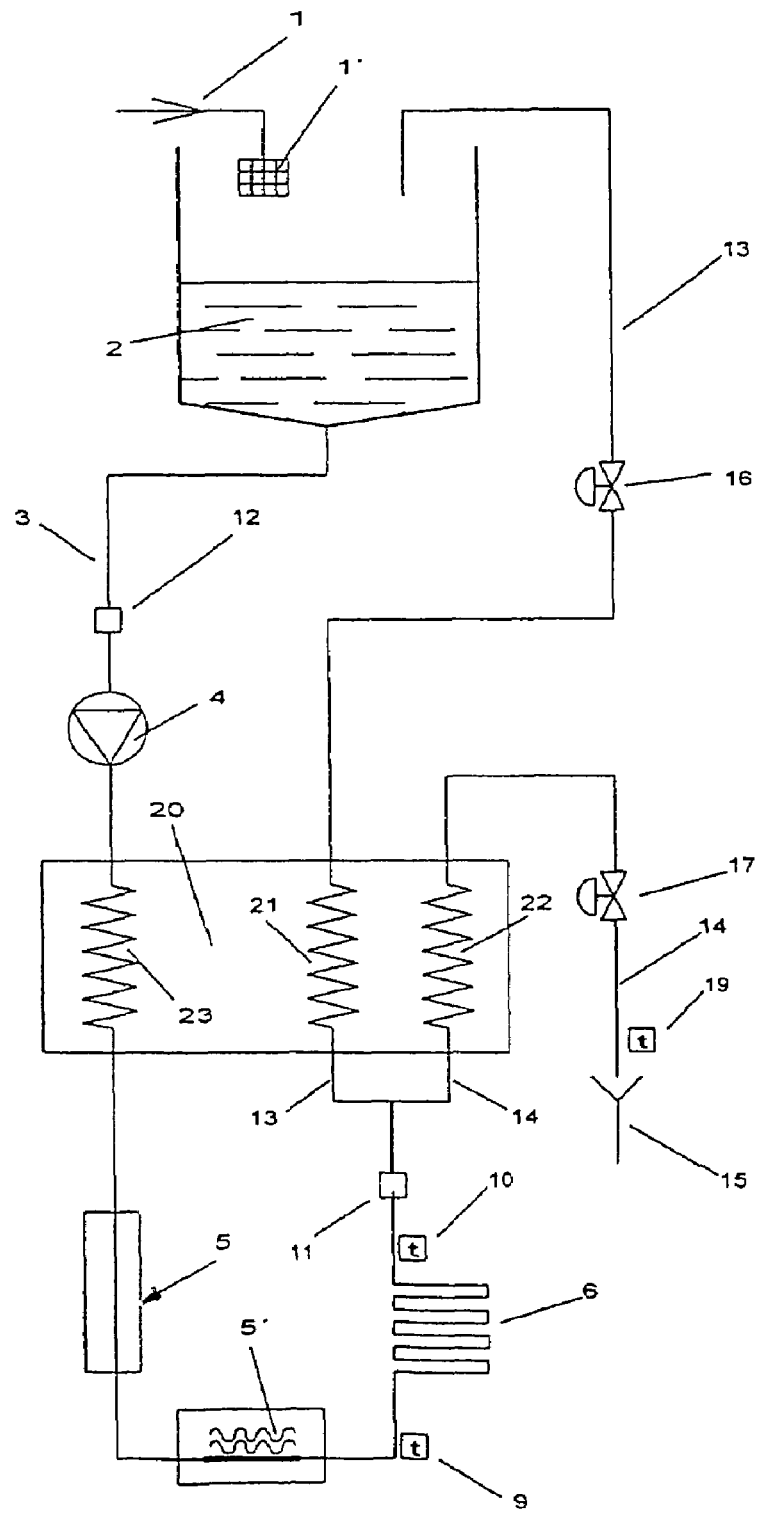
FIG. 2 is a schematic flow diagram of another embodiment of an apparatus for sterilizing, pasteurizing, and/or disinfecting pumpable or free flowing medium in accordance with the present invention.

Turning now to FIG. 2, there is shown a schematic flow diagram of another embodiment of an apparatus for sterilizing, pasteurizing, and/or disinfecting pumpable or free flowing medium in accordance with the present invention. Parts corresponding with those in FIG. 1 are denoted by identical reference numerals and not explained again. The description below will center on the differences between the embodiments. In this embodiment, provision is made for the arrangement of a heat exchanger 20, instead of the pumps 7, 8, for generating a resistance pressure to thereby regulate a flow of medium through one or the other conduit branches 13, 14. The heat exchanger 20 includes a heat exchanging coil 21 disposed in a portion of the conduit branch 13 and having a flow cross section which is smaller than the cross section of the conduit branch 13 upstream of the heat exchanging coil 21. Likewise, the heat exchanger 20 includes a heat exchanging coil 22 disposed in a portion of the conduit branch 14 and having a flow cross section which is smaller than the cross section of the conduit branch 14 upstream of the heat exchanging coil 22. Both heat exchanging coils 21, 22 guide incoming medium in counterflow to the flow of medium through a heat exchanging region 23 of the feed conduit 3, whereby the heat exchanging region 23 is hereby not reduced in cross section in relation to the feed conduit 3.

Operation of the apparatus of FIG. 2 is similar to the operation of the apparatus of FIG. 1, with the difference residing in the buildup of the resistance pressure, which in the embodiment of FIG. 2 is realized by the configuration of the heat exchanging coils 21, 22 which generate a pressure acting in opposition to the conveying pressure of the pump 4, as a result of the restriction, and measured by the pressure sensor 11. When starting the apparatus, shut-off member 17 in the conduit branch 14 to the outlet 15 is closed, whereas the shut-off member 16 in the conduit branch 13 to the storage tank 2 is open. Thus, the medium circulates until the medium has reached the desired temperature, as registered by the temperature sensor 10, and the desired pressure, as measured by the pressure sensor 11, to ensure that medium exiting the temperature holding device 6 is sufficiently decontaminated, i.e. sterilized, pasteurized or disinfected. Subsequently, the shut-off member 16 in the conduit branch 13 is closed and the shut-off member 17 in the conduit branch 14 is opened to allow a discharge of the decontaminated medium through the outlet 15. The temperature of outflowing medium is hereby monitored by the temperature sensor 19 to prevent overheating, when the medium exits through the outlet 15, and thereby prevent damage to the system.

It will be understood by persons skilled in the art that the temperature sensor 9 may be omitted in the apparatus according to the invention, by using the temperature, as determined by the temperature sensor 10, optionally also the pressure, as measured by the pressure sensor 11 and the flow rate, as determined by the flowmeter, to realize a sufficient supervision of the treatment temperature and treatment time.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein.

What is claimed is:

1. Apparatus for sterilizing, pasteurizing and/or disinfecting a pumpable or free-flowing medium, comprising:
    at least one heating source receiving medium via a feed conduit;
    a temperature sensor for monitoring a temperature of the medium along a temperature holding device downstream of the heating source;
    an outlet;
    a conveying member moving the medium to the temperature holding device and maintaining a feed pressure in the temperature holding device; and
    at least two conduits routed downstream from the temperature holding device, with one of the conduits communicating with the outlet, and with the other one of the conduits constituting a return conduit for returning the medium to the feed conduit, each conduits including
        a flow restriction member generating a resistance pressure in opposition to the feed pressure of the conveying member by restricting a passage for flow of medium, and
        a shutoff member for controlling a flow of fluid through the conduit, wherein the restriction member is part of a heat exchanger which guides medium from the temperature holding device in counterflow to a flow of medium to the heating source.

2. The apparatus of claim 1, wherein the restriction member includes a heat exchanging coil having a flow cross section which is smaller than a flow cross section of the conduit upstream of the restriction member.

3. The apparatus of claim 1, further comprising a flowmeter disposed in the feed conduit.

4. The apparatus of claim 1, further comprising a further temperature sensor disposed in the one of the conduits downstream of the restriction member.

5. The apparatus of claim 1, further comprising a pressure sensor disposed in a passageway between the conveying member and the restriction member.

* * * * *